United States Patent
Yan et al.

(10) Patent No.: US 11,497,890 B2
(45) Date of Patent: Nov. 15, 2022

(54) CATHETER SYSTEM

(71) Applicant: ORBUSNEICH MEDICAL (SHENZHEN) CO., LTD., Guangdone (CN)

(72) Inventors: Bryan Ping Yen Yan, Guangdone (CN); Lizhong Lu, Guangdone (CN); Junxiong Ouyang, Guangdone (CN)

(73) Assignee: ORBUSNEICH MEDICAL (SHENZHEN) CO., LTD., Guangdone (CN)

( * ) Notice: Subject to any disclaimer, the term of this patent is extended or adjusted under 35 U.S.C. 154(b) by 75 days.

(21) Appl. No.: 16/485,396

(22) PCT Filed: Aug. 27, 2018

(86) PCT No.: PCT/CN2018/102424
§ 371 (c)(1),
(2) Date: Aug. 12, 2019

(87) PCT Pub. No.: WO2019/184222
PCT Pub. Date: Oct. 3, 2019

(65) Prior Publication Data
US 2021/0213253 A1    Jul. 15, 2021

(30) Foreign Application Priority Data

Aug. 21, 2018   (CN) .......................... 201810956079.3

(51) Int. Cl.
*A61M 25/01* (2006.01)
*A61M 25/00* (2006.01)

(52) U.S. Cl.
CPC .... *A61M 25/0194* (2013.01); *A61M 25/0045* (2013.01); *A61M 25/0052* (2013.01);
(Continued)

(58) Field of Classification Search
CPC .......... A61M 25/0194; A61M 25/0045; A61M 25/0052; A61M 2025/0042;
(Continued)

(56) References Cited

U.S. PATENT DOCUMENTS

2010/0094258 A1*  4/2010  Shimogami ......... A61M 25/005
                                                    606/191
2013/0317528 A1*  11/2013  Anderson ......... A61M 25/0136
                                                    606/159

* cited by examiner

*Primary Examiner* — Laura A Bouchelle
*Assistant Examiner* — John A Doubrava
(74) *Attorney, Agent, or Firm* — Andrew F. Young; Nolte Lackenbach Siegel

(57) ABSTRACT

The present invention discloses a catheter system, comprising: a catheter head having a lumen, a proximal end and a distal end, and an opening positioned at a bottom of the distal end; and a rotatable inner tube having a lumen positioned in the lumen and at a proximal end of the catheter head, the inner tube including a front end having an arcuate opening; wherein the rotatable inner tube can be rotated so that the arcuate opening thereon can be made to engage or disengage with the opening at the bottom of the distal end of the catheter head. The invention also provides a catheter system and method for re-entry of a vascular false lumen into a true lumen in a quick, accurate and low-risk way. The catheter system for re-entry of a vascular false lumen into a true lumen in a quick, accurate and low-risk way effectively solve the problems of difficult operation, inaccurate positioning, long operation time and easiness to cause acute occlusion and internal hemorrhage of the branch vessel when the guidewire is re-entering the true lumen in the prior art.

38 Claims, 8 Drawing Sheets

(52) U.S. Cl.
CPC ............... *A61M 2025/0042* (2013.01); *A61M 2025/0197* (2013.01); *A61M 2210/125* (2013.01)

(58) Field of Classification Search
CPC .... A61M 2025/0197; A61M 2210/125; A61B 2017/22095
See application file for complete search history.

Section A-A

CATHETER SYSTEM

CROSS-REFERENCE TO RELATED APPLICATIONS

The present application is a national phase of Ser. No. PCT/CN2018/102424 filed Aug. 27, 2018, the entire contents of which are incorporated herein by reference, and which claims priority to and the benefit of Chinese Patent Application No. 201810956079.3 filed Aug. 21, 2018.

BACKGROUND OF THE INVENTION

1. Field of the Invention

The invention belongs to the field of interventional medical apparatus and instruments, and relates to a medical catheter system, and more particularly, to a catheter system and a method for re-entry of a vascular false lumen into a true lumen.

2. Description of the Related Art

Chronic total occlusion (CTO) lesions remain one of the challenges in percutaneous coronary intervention (PCI) due to its difficulty in surgery. However, with a deeper understanding of CTO lesions, and an accumulation of technical experience and an introduction of special devices, the success rate of PCI treatment in CTO lesions has been significantly improved, and PCI surgical techniques have become more standardized. Depending on the position of a working guidewire, PCI for CTO lesions comprises two techniques, namely, guidewire escalation techniques that directly reach the true lumen by passing through the plague in an occlusion segment and dissection and re-entry techniques (DART). Based on a direction along which the working guidewire passes through the CTO lesions, the above techniques, in effect, can be subdivided into two paths: forward and reverse paths.

The existing DART-related technologies mainly employ a forward-path guidewire that re-enters the true lumen via the false lumen. Subintimal tracking and re-entry (STAR) technology was the earliest DART technology, and was formally proposed by Colombo in 2005 (Colombo A, Mikhail G W, Michev I, et al. Treating chronic total occlusions using subintimal tracking and reentry: the STAR technique. *Catheter Cardiovasc Interv*, 2005, 64(4):407-411, 412.3). By using the STAR technology, the "key point" for the guidewire re-entering from the dissection to the true lumen is generally at the bifurcation of vessels beyond the occlusion segment, hence, a length of the false lumen will be significantly longer than distal fibrous caps, and acute occlusion of non-occluded branch vessels occurs. Another technique is Contrast-guided STAR technology (Contrast-guided STAR), which is a simplified STAR technology that was first proposed by Carlino in 2008 (Carlino M, Godino C, Latib A, et al. Subintimal tracking and re-entry technique with contrast guidance: a safer approach. *Catheter Cardiovasc Interv*, 2008, 72(6):790-796.36). It is also known as "improved STAR technology". Improved STAR concerns infusion of contrast agents in the occlusion segment using the microcatheter to separate the loose subintimal tissue and form a "visual" dissection to guide the working guidewire forward. Only when the standard forward or reverse technology fails is the re-entry technology (including classic and modified STAR technology) generally considered.

Another technique is mini-STAR technology or limited antegrade subintimal tracking technique (LAST), which is another improved STAR technology that was formally proposed by Galassi in 2012 (Galassi A R, Tomasello S D, Costanzo L, et al. Mini-STAR as bail-out strategy for percutaneous coronary intervention of chronic total occlusion. *Catheter Cardiovasc Interv*, 2012, 79(1):30-40.3). This technique, using FielderFC or XT Silk, is substantially the same to the classic STAR technology, except that the mini-STAR technology forms a shorter range of dissection, and the "penetration point" of the guidewire re-entering the true lumen is very close to the distal fiber caps of the CTO lesions. The Stingray system, produced by Boston Scientific, comprises a balloon and a guidewire. It is a special instrument designed for re-entry of the true lumen from the false lumen. Moreover, it can be used with the CrossBoss catheter or used alone. The BridePoint system, produced by Boston Scientific, consists of CrossBoss catheter, Stingray balloon and a guidewire. The BridePoint system, acts as a CTO-specific device of the forward path, and is mainly applicable to CTO lesions where the target vessels in the distal segment can be developed and have a relatively large diameter (Werner G S. The BridgePoint devices to facilitate recanalization of chronic total coronary occlusions through controlled subintimal reentry. *Expert Rev Med Devices*, 2011, 8(1):23-29.36).

At present, the main drawbacks of the above existing technology in which a forward-path guidewire re-enters the true lumen via the false lumen include: 1) when re-entering the true lumen, the guidewire is mostly located at the bifurcation of vessels beyond the occlusion segment, it is hard for a physician to accurately locate, so after the false lumen re-enters the true lumen, the length of the false lumen will be significantly longer than that of the distal fiber cap, and an acute occlusion of the non-occluded branch vessels occurs; 2) after the guidewire enters the middle vascular layer, during the process of pushing the guide wire by the physician, the guidewire is difficult to advance in a straight path, and the guidewire is easily bent or wrapped in the inner wall layer of the blood vessel or the vascular skin, i.e., Tunica externa. Tunica media, that can be penetrated due to an improper push force of the physician, leading to the result that a patient can suffer from an internal hemorrhage, in more serious cases, leading to the death of the patient; 3) the physician usually needs to spend a lot of operation time to use the existing tools to pass through the totally occluded area and help the guidewire re-enter the true lumen. The longer the operation time is, the greater the damage to the patient. Accordingly, there is a need for development of tools for assisting the physician in facilitating the guidewire to pass through the CTO lesions and directing the guidewire into the true lumen.

SUMMARY OF THE INVENTION

Aiming at the defects that the guidewire is difficult to operate, the positioning is inaccurate and the operation time is long and the interventional treatment has a high risk in the interventional treatment of guidewire, the main purpose of the invention is to provide a medical catheter system.

In order to solve the problems of difficult operation, inaccurate positioning, long operation time and easiness to cause acute occlusion and internal hemorrhage of the branch vessel when the guidewire is returned to the true lumen in the prior art, the present invention also provides a catheter system and a method for re-entry of a vascular false lumen into a true lumen in a quick, accurate and low-risk way.

In order to achieve the above purposes, the invention adopts the following technical solutions.

Embodiments of the present invention provide a catheter system, comprising a catheter head having a lumen, a proximal end and a distal end, and an opening positioned at a bottom of the distal end, and a rotatable inner tube having a lumen positioned in the lumen and at a proximal end of the catheter head, the inner tube including a front end having an arcuate opening. The rotatable inner tube can be rotated so that the arcuate opening thereon can be made to engage or disengage with the opening at the bottom of the distal end of the catheter head.

In certain embodiments, the catheter system further comprises a guidewire, located within the lumen of the rotatable inner tube. The rotatable inner tube can be rotated so that, depending on the engagement or disengagement between the arcuate opening of the inner tube and the opening of the catheter head, the guidewire penetrates downwards out of the opening along a guide path of the rotatable inner tube, or goes upwards into the lumen of the distal end of the catheter head along the guide path of the rotatable inner tube, respectively.

In some implementations, the opening of the catheter head includes a downwardly inclined first oblique shoulder. Upon a collusion between the guidewire and the first oblique shoulder along the guide path of the rotatable inner tube, the guidewire penetrates downwards out of the opening.

The catheter head can have a curved shape from the opening, and the lumen of the catheter head channel can include first and second parts, wherein the first part is slightly raised and the second part is horizontally arranged. In some implementations, the first part is raised upward about 2 to about 8 degrees and the second part is horizontally arranged. In further implementations, the angle between the first oblique shoulder and a vertical direction is about 30 to about 60 degrees. Upon a collision between the guidewire and the first oblique shoulder along the guide path of the rotatable inner tube, the guidewire can penetrate out of the opening at an angle of about 70 to about 90 degrees with respect to a horizontal plane.

A section of the arcuate opening can be inclined at an angle of about 2 to about 8 degrees with respect to the axis of the rotatable inner tube.

In some embodiments, the arcuate opening includes a distal end having an inclined second oblique shoulder, wherein the guidewire, upon a collision with the second oblique shoulder along the guide path, penetrates downwards out of the opening. The angle between the second oblique shoulder and a horizontal direction is can be about 15 to about 45 degrees. Upon collision between the rotatable inner tube and the second oblique shoulder along the guide path of the rotatable inner tube, the guidewire can penetrate out of the opening at an angle of about 70 to about 90 degrees with respect to a horizontal plane.

in some embodiments, the catheter system includes two streamlined wings arranged on opposite sides of the catheter head. The wings can be symmetrically disposed on the two sides of the catheter head, and the wings become wider and narrower gradually from front to back. The wings can be shaped by bending an arc at an angle of about 75 degrees to the sides of the catheter head.

In certain embodiments, the rotatable inner tube is rotatable 360° within the lumen of the catheter head. The catheter system can also include a support tube connected to the proximal end of the catheter head. The support tube can comprises a three-layer structure including an inner layer, an intermediate layer and an outer layer, wherein the inner layer is formed as a mesh structure and the intermediately layer is formed as a spiral structure. The catheter system can also include a tip connected to the distal end of the catheter head.

Embodiments of the present invention further provide a catheter system for re-entry of a vascular false lumen into a true lumen that comprises a curved catheter head having a lumen, a proximal end and a distal end, an opening at the bottom of the proximal end, and a downwardly first oblique shoulder, wherein the opening faces the first oblique shoulder and is positioned proximally with respect to the shoulder, and a rotatable inner tube having proximal end and a distal end, positioned within in the lumen and at a proximal end of the catheter head, the distal end of the rotatable inner tube having an arcuate opening. When the rotatable inner tube is rotated to a position where the arcuate opening faces upwards, a guidewire that is arranged within the lumen of the rotatable inner tube can enters the lumen of the distal end of the catheter head along a guide path of the rotatable inner tube. Alternatively, when the rotatable inner tube is rotated to a position where the arcuate opening faces downwards, a guidewire that is arranged within the lumen of the rotatable inner tube can penetrates downward out of the opening after collision with the first oblique shoulder along the guide path of the rotatable inner tube.

In certain embodiments, the lumen of the curved catheter head has a first part and a second part, wherein the first part is slightly raised upward about 3 to about 6 degrees and the other part is horizontally arranged. In certain implementations, the curved catheter head has an outer diameter of not more than about 0.54 mm and an inner diameter of about 0.48 mm. The maximum vertical height between a top and a bottom of the curved catheter head can be no greater than about 1 mm. The angle between the first oblique shoulder and a vertical direction can be about 45 degrees.

In further embodiments, the catheter system includes two streamlined wings arranged on opposite sides of the catheter head. In some implementations, the wings are symmetrically disposed on the opposite sides of the catheter head, and the wings become wider and narrower gradually from front to back. Each of the wings may be formed in the shape of an arc at an angle of about 75 degrees to the opposite sides of the catheter head. The width at a beginning of the distal section of the wings can be no greater than 0.9 mm and a maximum width of the wings can be no greater than 2.4 mm through extension. A maximum vertical height between the wings and the catheter head may be no greater than about 1.25 mm.

In some embodiments, the guidewire has a diameter between about 0.014 inches and about 0.018 inches.

The rotatable inner tube is preferably rotatable 360° within the lumen of the catheter head. Upon the guidewire colliding with the first oblique shoulder along the guide path of the rotatable inner tube, the guidewire penetrates out of the opening at an angle of about 70°-90° with respect to a horizontal plane. In some implementations, the arcuate opening of the rotatable inner tube is at an inclined angle of about 4°-5° with respect to an axial direction of the rotatable inner tube. The distal end of the rotatable inner tube can be made of nitinol and the proximal end of the rotatable inner tube can made of metal, and the distal and proximal ends can be integrally formed by welding.

The catheter system can also include a support tube connected to the proximal end of the catheter head. In some implementations, the support tube comprises a three-layer structure including an inner layer, an intermediate layer and an outer layer, wherein the inner layer is formed as a mesh structure and the intermediate layer is formed as a spiral structure. The wall of the support tube includes may have a thickness of about 0.004 inches.

A tip can be connected to the distal end of the catheter head.

Embodiments of the present invention also provide a method for re-entry of a vascular false lumen into a true lumen in a quick, accurate and low-risk way using a catheter head having a lumen, an opening and a first oblique shoulder, and a rotatable inner tube having a distal end with an arcuate opening, the inner tube positioned within the lumen of the catheter head. The method comprises rotating the rotatable inner tube to a position at which the arcuate opening faces upwards, inserting a first guidewire into the rotatable inner tube, pushing the first guidewire to the catheter head, such that the catheter head enters a region where a total occlusion of the false lumen of the vessel occurs, through a path to the false lumen created by the first guidewire, pushing a microcatheter until the catheter head passes through the totally occluded region in a straight line, and placing the first oblique shoulder of the catheter head on a position passing through the totally occluded region so as to withdraw the first guidewire, continually rotating the rotatable inner tube to a position at which the arcuate opening faces downwards, inserting a second guidewire into the rotatable inner tube, and pushing the second guidewire to the catheter head, such that the second guidewire penetrates downwards after a collusion with the first oblique shoulder on the catheter head, thereby re-entering to the vascular true lumen.

In some implementations of the method, the first guidewire has a diameter of about 0.018 inches. The second guidewire may have a diameter of about 0.014 inches. Upon the second guidewire colliding with the first oblique shoulder, the second guidewire penetrates out of the opening at an angle of about 70 to about 90 degrees with respect to a horizontal plane.

BRIEF DESCRIPTION OF THE DRAWINGS

The accompanying drawings, together with the specification, illustrate exemplary embodiments of the present disclosure, and, together with the description, serve to explain the principles of the present invention.

DETAILED DESCRIPTION

Figure 1:
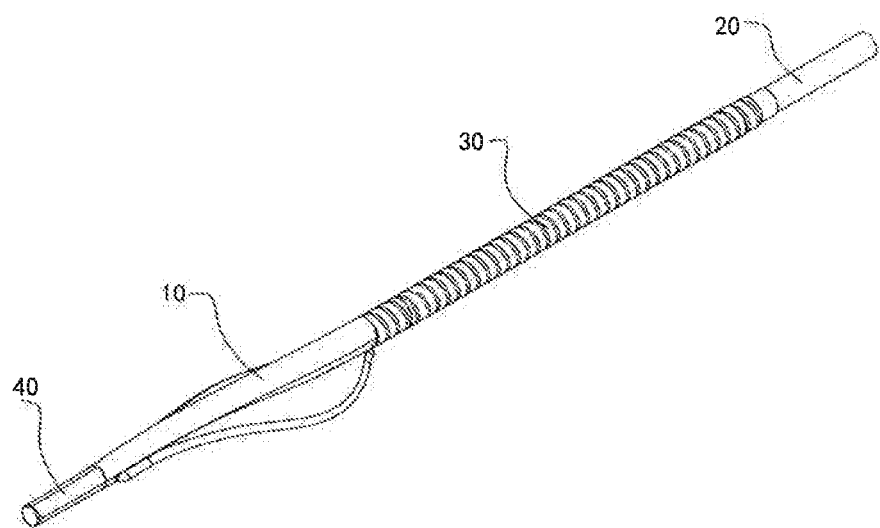
FIG. 1 is a schematic diagram of an overall structure of a catheter system according to the present invention.

The present invention will now be described more fully hereinafter with reference to the accompanying drawings, in which exemplary embodiments of the invention are shown. This invention may, however, be embodied in many different forms and should not be construed as limited to the embodiments set forth herein. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "plurality" means a number greater than one.

The terms "proximal" means located toward the operator of the catheter system and the term "distal" means located away from the operator of the catheter system.

Hereinafter, certain exemplary embodiments according to the present disclosure will be described with reference to the accompanying drawings.

The present invention provides a catheter system that can be widely used in interventional treatment of vascular lesions or interventional treatment of tumors. More specifically, the invention provides a catheter system and method for re-entry of a vascular false lumen into a true lumen in a quick, accurate and low-risk way. The catheter system reduces the physician's difficulty in operation, reduces operation time, and avoids causing acute occlusion and internal hemorrhage of the branch vessel.

For example, in vascular lesions, such as vascular stenosis and obstruction, renal artery, subclavian artery, iliac artery and lower limb atherosclerotic plaque stenosis, various aneurysms and arteriovenous malformations, femoral head necrosis caused by various reasons, interventional methods such as stenting, balloon dilatation, and endovascular embolization can significantly improve clinical symptoms of those vascular lesions. In the course of stenting or balloon dilation, the catheter system can help the physician pass through blocked lesion locations and complete the interventional treatment. For example, in a surgical treatment for chronic total occlusion of coronary artery, the catheter system provides a new path for a transmission and installation of the balloon and the stent by entering the false lumen through the guidewire; similarly, in the surgical treatment for chronic total occlusion of peripheral vessels, the catheter system provides a new path for a transmission and installation of the balloon and the stent by entering the false lumen through the guidewire.

In the interventional treatment of tumors (in particular for the treatment of all kinds of luminal stenosis diseases, such as blood vessels, biliary tract, digestive tract, trachea, urethra, etc, caused by postoperative or tumor compression), the catheter system may help the physician open up a new path for the interventional treatment, achieving precise chemotherapy for cancerous tissue, or help provide a fairly good path condition for stenting in narrow locations by opening up the new path to reduce surgical trauma; in the interventional treatment of tumors, the system is conducive to transporting embolic agent catheters to designated locations during the "embolization" process, and opens up new drug delivery paths by entering the false lumen before entering the true lumen, achieving accurate drug delivery and achieving the best therapeutic effect. In addition, the catheter system can be used for treatment of various tumors, benign or malignant.

Hereinafter, the present invention will be described in detail and specifically through specific embodiments so as to better illustrate the present invention, but the following embodiments do not limit the scope of the present invention.

As shown in FIGS. 1 to 4, the present invention provides a catheter system that includes a catheter head 10 having an opening 11 positioned at the bottom and toward the proximal end of the catheter head, a rotatable inner tube 20, located in a lumen of the distal end of the catheter head 10, the distal end of the rotatable inner tube 20 being provided with an arcuate opening 21, wherein the rotatable inner tube 20 is rotatable 360° in the lumen of the catheter head 10 to achieve a path-selection and allowing different guidewires to enter fixed lumens. The rotatable inner tube 20 can be rotated so that the arcuate opening 21 thereon is in communication with or disengaged from the opening 11 at the bottom of the catheter head 10. Moreover, the catheter system further comprises a guidewire 50 (shown in FIGS. 21 and 22), located in a lumen of the rotatable inner tube 20, wherein when in use, once the rotatable inner tube 20 is rotated to a position where the arcuate opening 21 faces upwards, the guidewire 50 can enter into the lumen of the distal end of the catheter head 10 along the guide path of the rotatable inner tube 20. Once the rotatable inner tube 20 is rotated to a position where the arcuate opening 21 faces downwards, the guidewire 50 can penetrate downwards out of the opening 11 along the guide path of the rotatable inner tube. The catheter system can be widely used in the above treatment of all kinds of vascular diseases or in the interventional treatment of tumors.

In certain embodiments, the edges and/or perimeter of the arcuate opening 21 is a U-shaped structure, arranged obliquely along the guide path of the rotatable inner tube 20. The edges or the perimeter of the arcuate opening 21 can be a triangular structure with curvilinear lines, thereby forming a generally triangular opening. In addition, the opening of the arcuate opening 21 may take other forms, for example, semi-circular, ovoid, semi-ovoid, rectangular or semi-rectangular shapes. In practice, the shape and the dimensions of the arcuate opening 21 may be adjusted to accommodate different types of medical devices, for example, to accommodate guidewires with diameters ranging from about 0.05 mm to about 1.0 mm. Specifically, the opening shape of the arcuate opening 21 may be varied depending on the form of the tip of the guidewire and the diameter of the guidewire.

In one embodiment, as shown in FIGS. 2, 4, 7 and 8, a downwardly inclined first oblique shoulder 12 is disposed on the opening 11 along a direction of the catheter head 10, and after a collision with the first oblique shoulder 12 along the guide path of the rotatable inner tube 20, the guidewire 50 penetrates downwards out of the opening 11. The purpose of the first oblique shoulder 12, which may have an inclination angle ranging from about 30° to 60°, is to urge the guidewire 50 protruding from the guide path of the rotatable inner tube 20 to change a direction and penetrate downwards out of the opening 11, which is conductive to pushing the guidewire and reducing the difficulty of operation when conducted by the physician.

Figure 2:
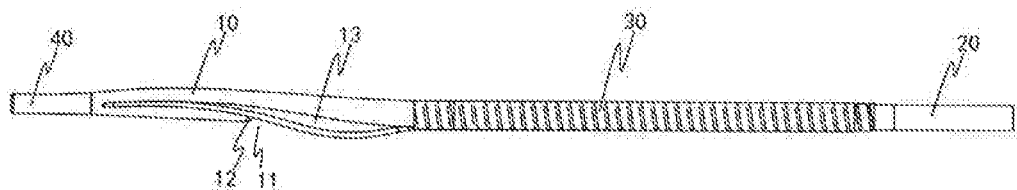
FIG. 2 is a front view of a catheter system according to the present invention.
Figure 3:
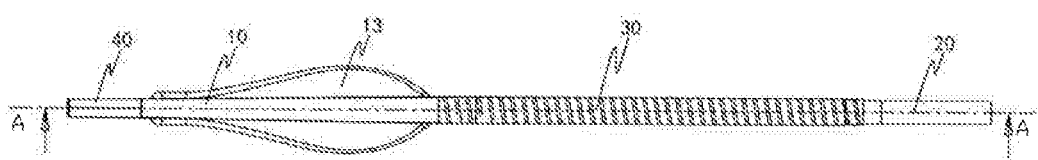
FIG. 3 is a schematic top view of a catheter system according to the present invention.

In the embodiment shown in FIGS. 1 and 2, the catheter head 10 has a curved shape from the opening 11, and its lumen channel has two parts, wherein one part is slightly raised and the other part is horizontally arranged. In some implementations, the slightly raised part is raised upward about 2 to 8 degrees, preferably 3 to 6 degrees, and more preferably by about 4.2 degrees, and the other part is horizontally arranged. In such embodiments, the first inclined shoulder 12 may have an angle of about 30-60°, preferably about 35-58°, about 40-55°, and about 42-55° to the vertical direction. In some implementations, the first inclined shoulder 12 is at an angle of about 45° to the vertical direction. On the basis of the inclination angle of the first oblique shoulder 12, after collision with the first oblique shoulder 12 along the guide path of the rotatable inner tube 20, the guidewire can penetrate out of the opening 11 at an angle of about 70°-90°, preferably 72°-88°, 75°-85°, 78°-85°, and more preferably about 80°-82° with respect to the horizontal plane. In addition, the upwardly-raised catheter head 10 can be raised so that its lumen is also raised upwards, and the upwardly-raised upper lumen can receive and convey a guidewire of about 0.018 inches in diameter. The distal end of the arcuate opening 21 facing the first oblique shoulder 12 at the angle of about 45° is used as the collision surface. A second guidewire of about 0.014 inches in diameter can be pushed to the collision surface and may change the direction and penetrate out of the opening 11 at a relatively larger angle of about 75°-90° with respect to the horizontal plane.

As a preferred embodiment, a section of the arcuate opening 21 is at an angle of inclination of about 2-8°, preferably 4-6°, and more preferably about 4.8°, in the direction of the rotatable inner tube 20. The distal end of the rotatable inner tube 20 may be made of nickel-titanium alloy, so as to ensure the strength of the guide path of the rotatable inner tube and reduce the possibility of deflection of the path; the proximal end of the rotatable inner tube may be made of metal, such as 304 stainless steel; and the distal end can be integrally formed with the proximal end by welding, such as by laser welding.

Figure 11:
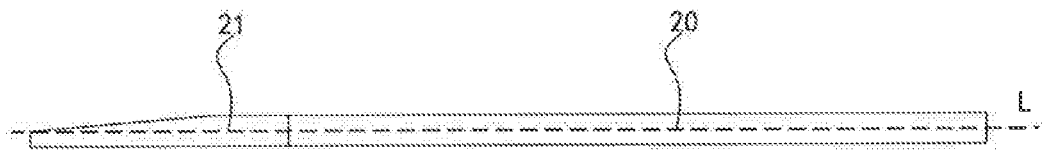
FIG. 11 is a schematic diagram of a front view of a rotatable inner tube in a catheter system according to the present invention.
Figure 12:
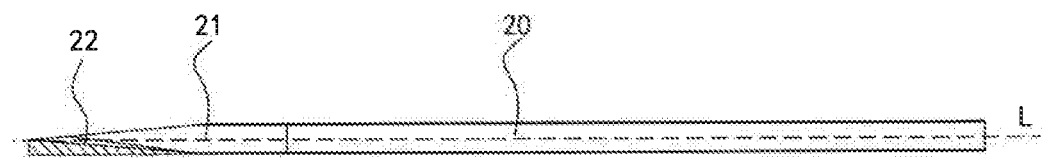
FIG. 12 is a schematic sectional view of a rotatable inner tube in a catheter system according to the present invention.
Figure 13:
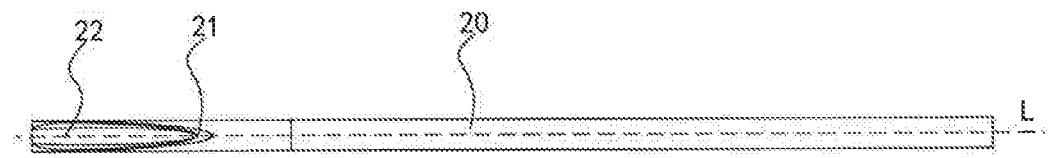
FIG. 13 is a schematic top view of a rotatable inner tube in a catheter system according to the present invention.
Figure 22:
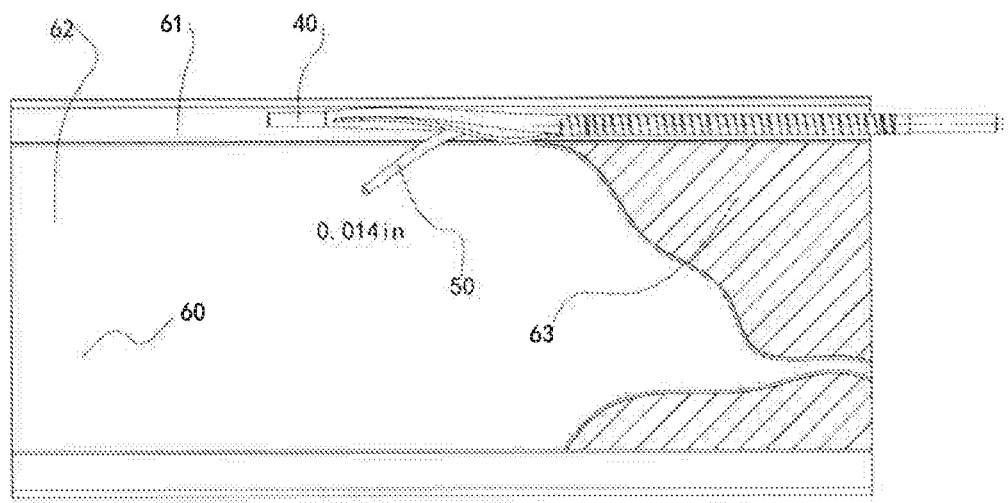
FIG. 22 is a schematic view of another working state of a catheter system in a vascular false lumen according to the present invention.

In another preferred embodiment, as shown in FIGS. 11 to 13, a distal end of the arcuate opening 21 is provided with an inclined second oblique shoulder 22, and after a collision with the second oblique shoulder 22 along the guide path of the rotatable inner tube 20, the guidewire penetrates downwards out of the opening 11, wherein in this embodiment, the guide path of the rotatable inner tube 20 is in the direction of the longitudinal axis L of the rotatable inner tube 20. The second oblique shoulder 22 may be at an angle of about 15-45°, preferably 18-42°, 20-40°, 20-38°, 22-35°, and more preferably about 25-30° to a horizontal direction. The angle between the second oblique shoulder 22 and the horizontal plane is smaller than the angle between the first oblique shoulder 12 and the horizontal plane, such that the guidewire 50 may smoothly transition from the guide path of the rotatable inner tube 20 to the first oblique shoulder 12 via the second oblique shoulder 22. In this embodiment, after the collision with the second oblique shoulder 22 along the guide path of the rotatable inner tube, the guidewire may penetrate out of the opening 11 at an angle of about 70°-90°, preferably 72°-88°, 75°-85°, 78°-85°, and more preferably about 80°-82° with respect to the horizontal plane, as shown in FIG. 22.

As shown in FIGS. 1 to 17, the catheter system further comprises two streamlined wings 13 arranged on either side of the catheter head 10, and the thickness of the wing may range from 0.075 mm to 0.1 mm. Each wing 13 is deployed to both sides from a center shaft toward a tip. The thickness of the wing decreases from the center toward the tip. The wings 13 are symmetrically disposed on the two sides of the catheter head 10, and the wings 13 also widen in span toward a distal end, to form a streamlined structure. The wing 13 may be shaped by bending an arc at an angle ranging from 60° to 80°, preferably 75°, to both sides from the central axis of the catheter. In this embodiment, the structure of the wing 13 is designed to help the physician to push the catheter head 10 into the vascular false lumen, and help the microcatheter advance along a straight path to reduce the risk of perforation of the outer layer of the blood vessel. This measure helps prevent the microcatheter from traveling along a spiral path. Moreover, the microcatheter is attached to the false lumen for holding the microcatheter in position and preventing the microcatheter from slipping or ectopia. Thereby, the difficulty in operation is decreased and the operation time is reduced.

Figure 18:
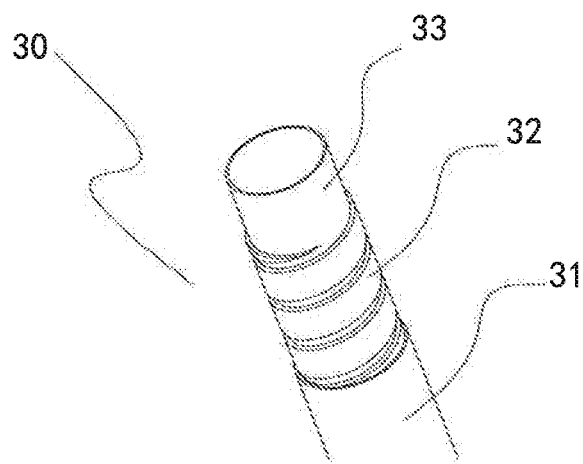
FIG. 18 is a schematic diagram of a support tube in a catheter system according to the present invention.
Figure 19:
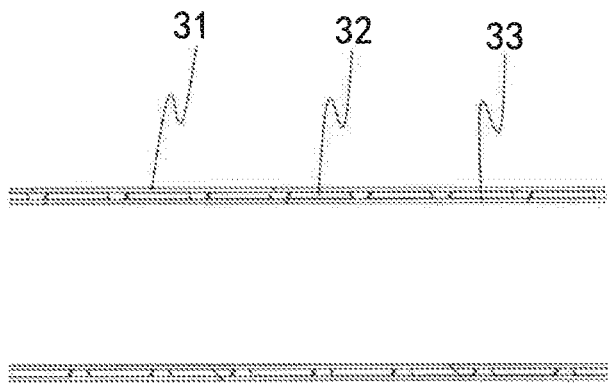
FIG. 19 is a schematic sectional view of a support tube in a catheter system according to the present invention.

In FIGS. 1 to 8, the catheter system further comprises a support tube 30 connected to the proximal end of the catheter head 10, e.g., by welding. As shown in FIGS. 18 and 19, the support tube 30 may be a three-layer structure composed of an inner layer 33, an intermediate layer 32, and an outer layer 31, and the inner layer 33 and the intermediate layer 32 may be composed of either a mesh or a spiral structure. The outer layer 31 may be firmed of nylon, or other preferable polymer materials; the intermediate layer 32 can be a hypotube layer, the surface structure of which may be mesh or spiral, formed by cutting of a laser machine; the inner layer 33 structure can also be a mesh or spiral structure; the intermediate layer and the inner layer may be made of a metal material, wherein the metal material is preferably a stainless steel/nickel alloy.

The catheter system further comprises a tip 40 which may be welded to the catheter head 10. The tip 40 and the catheter head 10 may be formed through injection molding of a polymer material. The polymer material used is preferably durable. Example polymers that are suitable may include one or more of ABS (ABS resin), PLA (polylactic acid), PVA (polyvinyl alcohol), PTFE (polytetrafluoroethylene), and Nylon.

The present invention provides a catheter system for re-entry of a vascular false lumen into a true lumen in a quick, accurate and low-risk way. The catheter system includes a curved catheter head 10 having an opening 11 at the bottom of its rear end, the opening 11 facing a downwardly inclined first oblique shoulder 12 in the direction of the catheter head 10; a rotatable inner tube 20, located in the lumen of the rear end of the catheter head 10, the distal end of the rotatable inner tube 20 being provided with an arcuate opening 21, and the rotatable inner tube 20 is 360-degree rotatable in the lumen of the catheter head 10 to allow different guidewires to enter the fixed lumens. When the rotatable inner tube 20 is rotated to a position at which the arcuate opening 21 faces upwards, a guidewire, arranged in the rotatable inner tube 20 can enter into the lumen of the distal end of the catheter head 10 along the guide path of the rotatable inner tube 20. Alternatively, when the rotatable inner tube 20 is rotated to a position where the arcuate opening 21 faces downwards, the guidewire, arranged in the rotatable inner tube 20, may penetrate downwards out of the opening 11 after collision with the first oblique shoulder 12 along the guide path of the rotatable inner tube 20.

Referring to FIGS. 1 to 17, the lumen channel of the curved catheter head 10 has two parts, wherein one part is slightly raised upward about 3 to 6 degrees, preferably 3.4 to 5.3 degrees, and more preferably by about 4.2 degrees, and the other part is horizontally arranged. As shown in FIG. 10, the curved catheter head 10 may have an inner diameter (R1) of about 0.48 mm, and an outer diameter (R2) of not more than about 0.54 mm, and preferably about 0.51 mm. In some embodiments, a maximum vertical height (d3) between a top of the catheter head 10 and a bottom of the first oblique shoulder 12 may be about 0.82 mm, although other values may be used, and, in some embodiments, the maximum vertical height (d4) between the top and a bottom of the curved catheter head 10 is not more than about 1 mm. In a particular embodiment, the upwardly-raised catheter head 10 is raised so that its lumen is also raised upwards, and the upwardly-raised upper lumen can receive and convey a first guidewire having a diameter of about 0.018 inches. The distal end of the arcuate opening 21 facing the first oblique shoulder 12 at the angle of 45 degrees is used as a guidewire collision surface, enabling a second guidewire of about 0.014 inches in diameter to be pushed to the collision surface, such that the guidewire may change the direction and re-enter the true lumen at a relatively larger angle of 75°-90° with respect to the horizontal plane.

Figure 4:
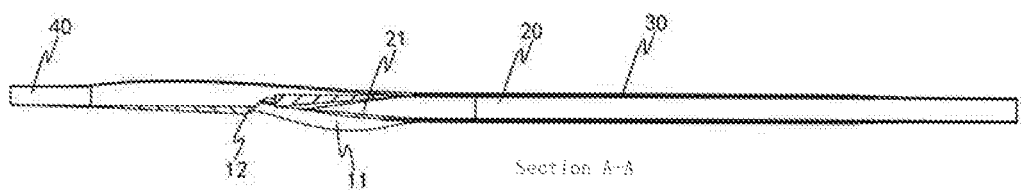
FIG. 4 is a sectional view of a catheter system according to the present invention.
Figure 5:
FIG. 5 is a schematic diagram for assembly of a catheter system according to the present invention.
Figure 6:
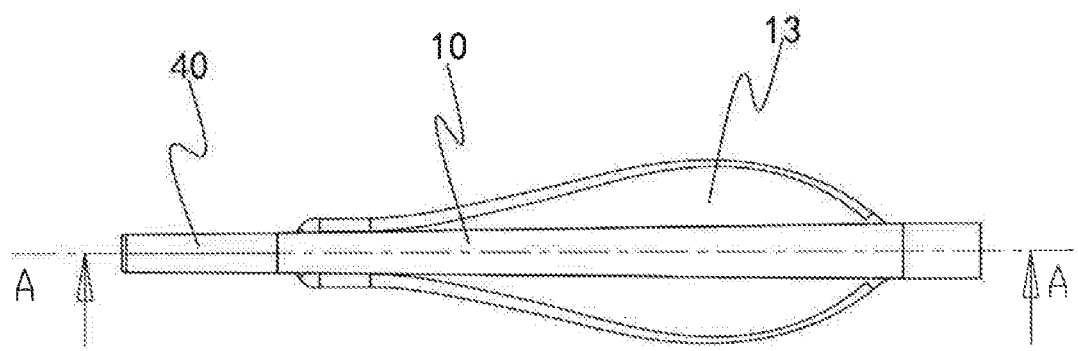
FIG. 6 is a schematic top view of a catheter head in a catheter system according to the present invention.
Figure 7:
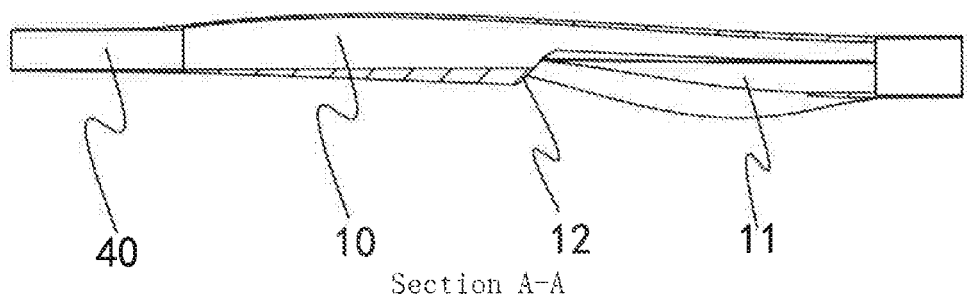
FIG. 7 is a schematic sectional view of a catheter head in a catheter system according to the present invention.
Figure 8:
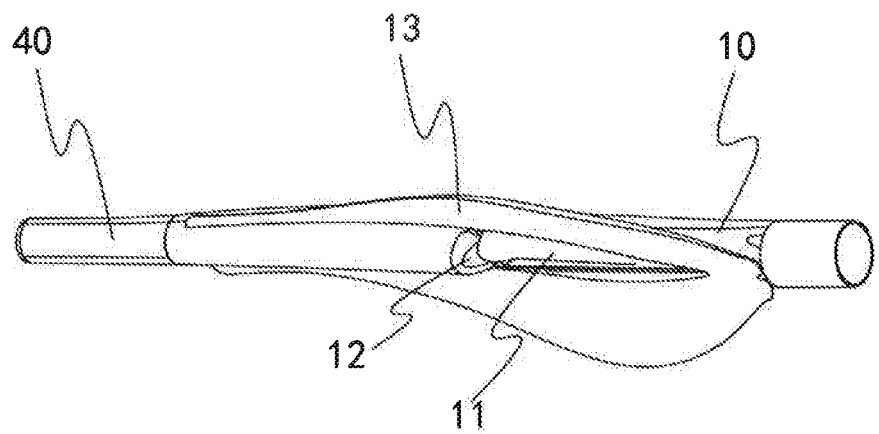
FIG. 8 is a schematic bottom view of a catheter head in a catheter system according to the present invention.

As shown in FIG. 4, the first oblique shoulder 12 may be at an angle of about 30-60°, preferably 35-58°, 40-55°, 42-55°, and more preferably about 45° to the vertical direction. After collision with the first oblique shoulder 12 along the guide path of the rotatable inner tube 20, the guidewire may penetrate out of the opening 11 at an angle of about 70°-90°, preferably 72°-88°, 75°-85°, 78°-85°, and more preferably about 80°-82° with respect to the horizontal plane, and re-enter the vascular true lumen.

The embodiments shown in FIGS. 1 to 17 provide a catheter system for facilitating a quick, accurate and low-risk re-entry of a vascular false lumen into a true lumen in a quick, accurate and low-risk way. The catheter further comprises two wings 13 arranged on two sides of the catheter head 10 in a streamlined design. The wings 13 are symmetrically disposed on the two sides of the catheter head 10, and the wings 13 become wider and narrower gradually from a distal section toward a proximal section. The thickness of the wing can range from 0.075 mm to 0.1 mm. The wing is deployed to both sides from a center shaft and the thickness of the wing may decreases toward its extremities. The wing 13 may be shaped by bending an arc at an angle ranging from about 60° to 80°, preferably about 75°, to two sides.

Figure 9:
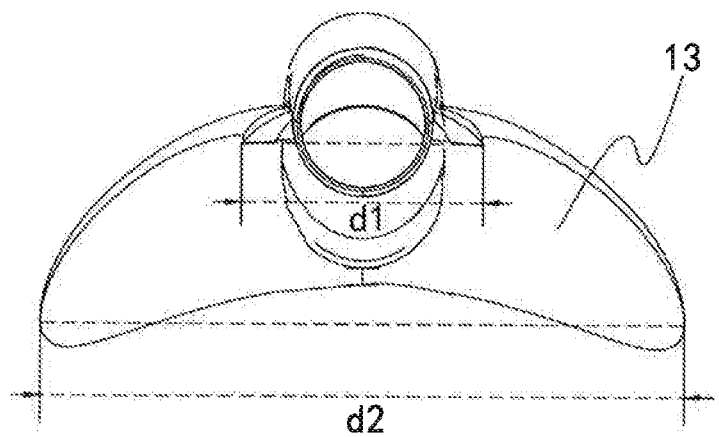
FIG. 9 is a schematic diagram of a width of a thin wing in a catheter system according to the present invention.
Figure 10:
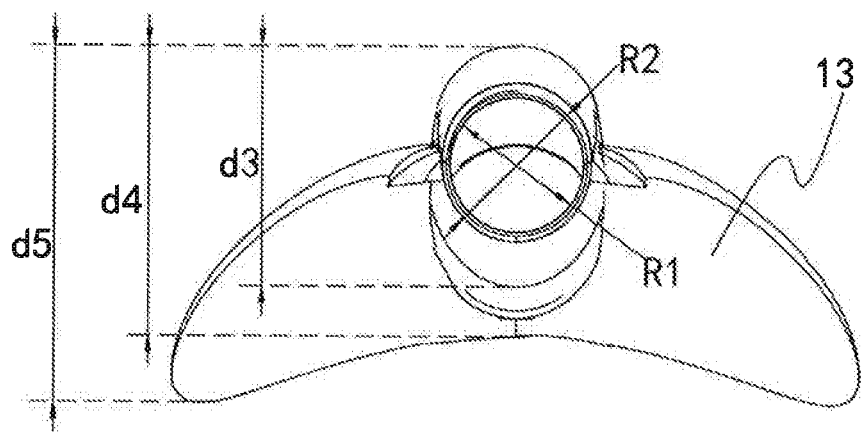
FIG. 10 is a schematic diagram of a height of a catheter head in a catheter system according to the present invention.

In the embodiment shown in FIG. 9, the width (d1) at the beginning of the front end of the wing 13 may be no greater than about 0.9 mm, and preferably about 0.88 mm, and a maximum width of the wings may be no greater than 2.4 through extension, and preferably about 2.34 mm. As shown in FIG. 10, the maximum vertical height (d5) between the wing 13 and the catheter head 10 may be no greater than 1.25 mm, and preferably about 1.22 mm.

The catheter systems for re-entry of a vascular false lumen into a true lumen in a quick, accurate and low-risk way according to the present invention may be particularly adapted for deploying a guiding wire having a diameter in a range of about 0.014 inches to about 0.018 inches.

After the collision with the first oblique shoulder 12 along the guide path of the rotatable inner tube 20, the guidewire may penetrate out of the opening 11 at an angle of about 70°-90° with respect to the horizontal plane. As shown in FIGS. 11 to 13, the inclination angle of the arcuate opening 21 may be between 4°-5°, preferably about 4.8°, in the direction of the rotatable inner tube 20. The distal end of the rotatable inner tube 20 may be made of a nickel-titanium alloy, so as to ensure the strength of the guide path of the rotatable inner tube and reduce the possibility of deflection of the path; the proximal end may be made of metal, such as 304 stainless steel. The distal end of the rotatable inner tube 20 may be integrally formed with the proximal end by welding, such as by laser welding.

Figure 14:
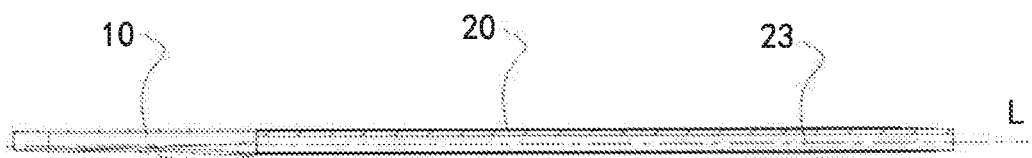
FIG. 14 is a schematic diagram of an eccentric circular channel of the rotatable inner tube facing downward in a catheter system according to the present invention.
Figure 15:
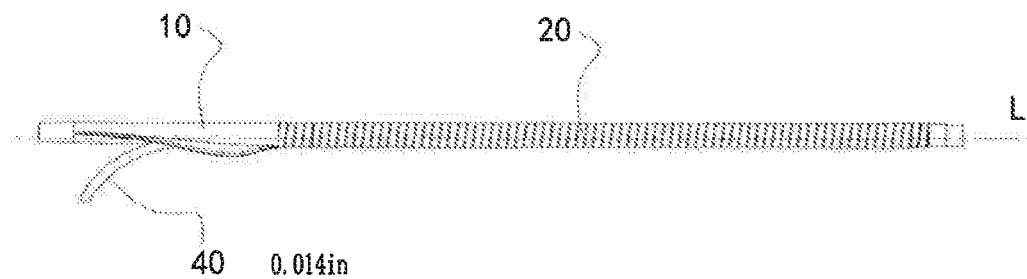
FIG. 15 is a schematic diagram of the working state of the guidewire when the eccentric circular channel of the catheter system, shown in FIG. 14, faces downward.
Figure 16:
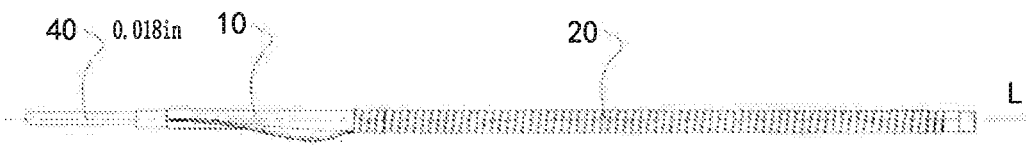
FIG. 16 is a schematic diagram of an eccentric circular channel of the rotatable inner tube facing upward in a catheter system according to the present invention.
Figure 17:
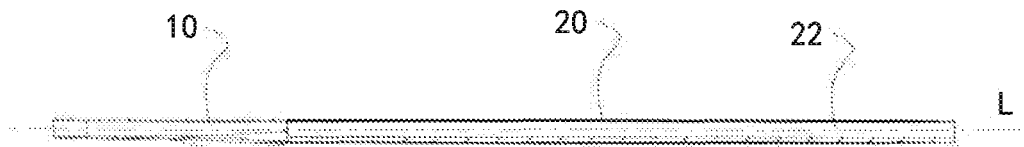
FIG. 17 is a schematic diagram of the working state of the guidewire when the eccentric circular channel of the catheter system, shown in FIG. 16, faces upward.

The rotatable inner tube 20 used in the technical solution may have an eccentric circular channel 23. By rotating the rotatable inner tube 20 having the eccentric circular channel 23, guidewires of different sizes may be enabled to enter the specific catheter head channel in the direction of the longitudinal axis L of the rotatable inner tube 20. In this manner, reentry of the guide path and the penetration false lumen into the true lumen can be achieved. When the rotatable inner tube 20 is rotated to so that the eccentric circular channel 23 faces downward, the guidewire may penetrate downward out of the vascular false lumen from the opening 11. and into the vascular true lumen after a collision with the first oblique shoulder 12 along the guide path formed along the eccentric circular channel 23 of the rotatable inner tube 20. A schematic diagram showing a first guidewire having a 0.018 inch diameter is shown in FIGS. 14 and 15. Alternatively, when the rotatable inner tube 20 is rotated to so that the eccentric circular channel 23 faces upward, a second, smaller guidewire of 0.014 diameter can enter the lumen of the catheter head 10 at a front end along the guide path L of the rotatable inner tube 20. A schematic diagram of a guidewire having a 0.014 inch diameter is shown in FIGS. 16 and 17.

A support tube 30 can be connected to the proximal end of the catheter head 10 by welding. As shown in FIGS. 18 to 19, the support tube 30 can be implemented as a three-layer structure composed of an inner layer 33, an intermediate layer 32, and an outer layer 31. The inner layer 33 and the intermediate layer 32 can be in a mesh and/or spiral structures. The outer layer may be formed of nylon, or other polymer materials. In some implementations, the intermediate layer is a hypotube layer, the surface structure of which may be mesh or spiral, formed by cutting of a laser machine. In some implementations, the inner layer structure is a mesh or spiral structure. The intermediate layer and the inner layer are made of a metal material, such as a stainless steel/nickel alloy.

A tip 40 can be welded to the catheter head 10. The tip 40 and the catheter head 10 may be formed through injection molding by a polymer material. The tip 40 can playing a guiding role, increasing passage and reducing vascular injury. The polymer material of the microcatheter head is designed to be durable. The polymer material, can be selected from one or more of ABS (ABS resin), PLA (polylactic acid), PVA (polyvinyl alcohol), PTFE (polytetrafluoroethylene), and Nylon.

Figure 20:
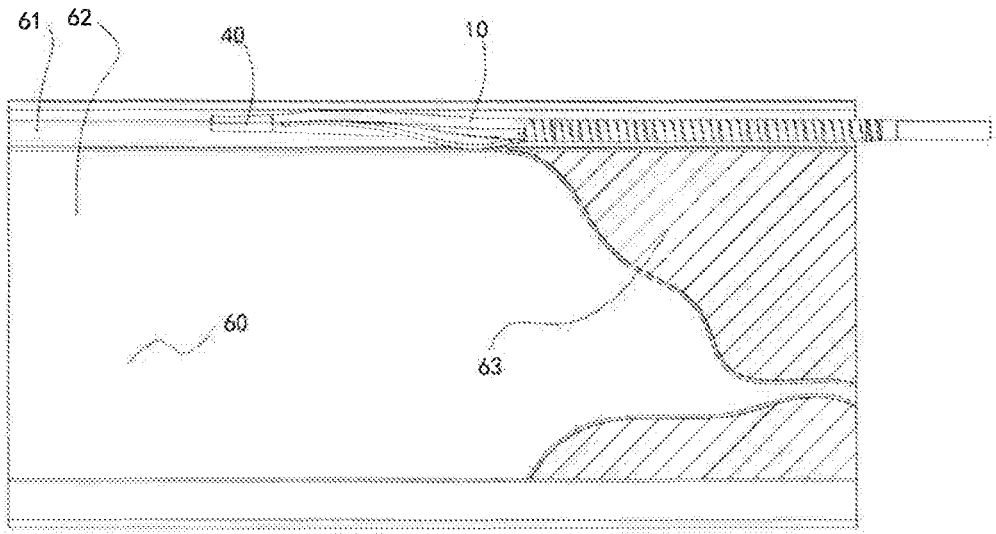
FIG. 20 is a schematic diagram of a state where a catheter system passes through a totally occluded region according to the present invention.
Figure 21:
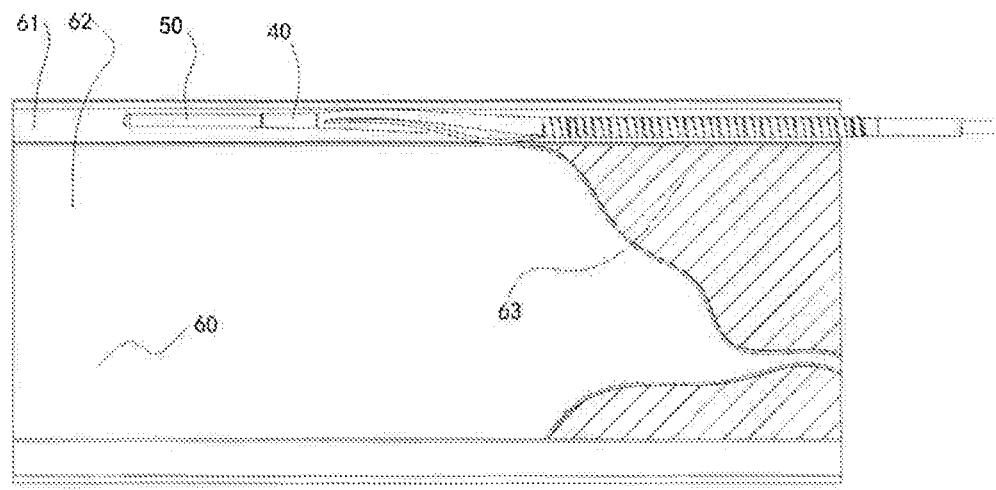
FIG. 21 is a schematic view of one working state of a catheter system in a vascular false lumen according to the present invention.

The embodiment provides a method for re-entry of a vascular false lumen into a true lumen in a quick, accurate and low-risk way by using the abovementioned catheter system, comprising:

Step 1, as shown in FIG. 20, comprises inserting the catheter system into the vascular false lumen 61 of the blood vessel 60, and rotating the rotatable inner tube to a position where the beak-shaped opening faces upwards, and inserting a first guidewire 50 having a diameter of about 0.018 inches into the rotatable inner tube 20 and pushing the same to the catheter head 10 first, such that the catheter head 10 enters into a region 63, where a total occlusion of the vascular false lumen occurs, through a path to the false lumen, wherein the path is laid by a first guidewire 50, as shown in FIG. 21.

Step 2 comprises pushing a microcatheter until the catheter head 10 passes through the totally occluded region 63 in a straight line, and placing the first oblique shoulder 12 on the catheter head 10 on a position just passing through the totally occluded region, so as to withdraw the first guidewire 50.

Step 3, as shown in FIG. 22, comprises rotating the rotatable inner tube 20 to a position at which the arcuate opening 21 faces downwards, and inserting a second guidewire 50 having a diameter of about 0.014 inches into the rotatable inner tube and pushing the same to the catheter head 10, such that the second guidewire 50 penetrates out of the opening 11 and into the vascular true lumen 62 at the angle of 70°-90° to the horizontal plane after a collusion with the first oblique shoulder 12 on the catheter head 10. As for the method, it is simple to operate and is of high efficiency. Moreover, accurate positioning can be ensured during the period of the guidewire re-entering the true lumen, thereby avoiding acute occlusion and internal hemorrhage of the branch vessel.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:
1. A catheter system, comprising:
   a catheter head having a lumen, a proximal end and a distal end, and an opening positioned at a bottom of the catheter head;

a rotatable inner tube having a lumen positioned in the lumen and at the proximal end of the catheter head, the inner tube including a front end having an arcuate opening; and a guidewire, located within the lumen of the rotatable inner tube;

wherein, the rotatable inner tube can be rotated so that the arcuate opening thereon can be made to engage or disengage with the opening at the bottom of the catheter head of the catheter head, wherein the rotatable inner tube can be rotated so that, depending on the engagement or disengagement between the arcuate opening of the inner tube and the opening of the catheter head, the guidewire penetrates downwards out of the opening along a guide path of the rotatable inner tube, or goes upwards into the lumen of the distal end of the catheter head along the guide path of the rotatable inner tube, respectively.

2. The catheter system as claimed in claim 1, wherein the opening of the catheter head includes a downwardly inclined first oblique shoulder;

wherein when the guidewire collides with the first oblique shoulder along the guide path of the rotatable inner tube, the guidewire penetrates downwards out of the opening.

3. The catheter system as claimed in claim 1, wherein a section of the arcuate opening is at an angle of inclination of about 2 to about 8 degrees along an axial direction of the rotatable inner tube.

4. The catheter system as claimed in claim 1, wherein the front end of the rotatable inner tube thas an inclined second oblique shoulder positioned at a distal end of the arcuate opening;

wherein the guidewire, upon a collision with the second oblique shoulder along the guide path, penetrates downwards out of the opening.

5. The catheter system as claimed in claim 1, further comprising:

two streamlined wings arranged on opposite sides of the catheter head.

6. The catheter system as claimed in claim 1, wherein the rotatable inner tube is rotatable 360° within the lumen of the catheter head.

7. The catheter system as claimed in claim 1, further comprising:

a support tube, connected to the proximal end of the catheter head.

8. The catheter system as claimed in claim 1, further comprising:

a tip, connected to the distal end of the catheter head.

9. The catheter system as claimed in claim 2, wherein the catheter head has a curved shape from the opening, and the lumen of the catheter head has first and second parts, wherein the first part is slightly raised and the second part is horizontally arranged.

10. The catheter system as claimed in claim 2, wherein an angle between the first oblique shoulder and a vertical direction is about 30 to about 60 degrees.

11. The catheter system as claimed in claim 2, wherein after the collision with the first oblique shoulder along the guide path of the rotatable inner tube, the guidewire penetrates out of the opening at an angle of about 70 to 90 degrees with respect to a horizontal plane.

12. The catheter system as claimed in claim 9, wherein first part is slightly raised upward about 2 to about 8 degrees and the second part is horizontally arranged.

13. The catheter system as claimed in claim 4, wherein an angle between the second oblique shoulder and a horizontal direction is about 15 to about 45 degrees.

14. The catheter system as claimed in claim 4, wherein upon collision between the second oblique shoulder of the rotatable inner tube along the guide path of the rotatable inner tube, the guidewire penetrates out of the opening at an angle of about 70 to about 90 degrees with respect to a horizontal plane.

15. The catheter system as claimed in claim 5, wherein the wings are symmetrically disposed on the two sides of the catheter head, and the wings become wider and narrower gradually from front to back.

16. The catheter system as claimed in claim 6, wherein the support tube comprises a three-layer structure including an inner layer, an intermediate layer and an outer layer, wherein the inner layer is formed as a mesh structure and the intermediately layer is formed as a spiral structure.

17. A catheter system for re-entry of a vascular false lumen into a true lumen, comprising:

a curved catheter head having a lumen, a proximal end and a distal end, an opening at the bottom of the proximal end, and a downwardly first oblique shoulder, wherein the opening faces the first oblique shoulder and is positioned proximally with respect to the shoulder; and a rotatable inner tube having a proximal end and a distal end, positioned within the lumen and at the proximal end of the catheter head, the distal end of the rotatable inner tube having an arcuate opening;

wherein when the rotatable inner tube is rotated to a position where the arcuate opening faces upwards, a guidewire that is arranged within the lumen of the rotatable inner tube can enter the lumen of the distal end of the catheter head along a guide path of the rotatable inner tube;

wherein when the rotatable inner tube is rotated to a position where the arcuate opening faces downwards, a guidewire that is arranged within the lumen of the rotatable inner tube can penetrate downward out of the opening after collision with the first oblique shoulder along the guide path of the rotatable inner tube.

18. The catheter system as claimed in claim 17, wherein the lumen of the curved catheter head has a first part and a second part, wherein the first part is slightly raised upward about 3 to about 6 degrees and the other part is horizontally arranged.

19. The catheter system as claimed in claim 17, wherein an angle between the first oblique shoulder and a vertical direction is about 45 degrees.

20. The catheter system as claimed in claim 17, further comprising:

two streamlined wings arranged on opposite sides of the catheter head.

21. The catheter system as claimed in claim 17, wherein the guidewire has a diameter between about 0.014 inches and about 0.018 inches.

22. The catheter system as claimed in claim 17, wherein the rotatable inner tube is rotatable 360° within the lumen of the catheter head.

23. The catheter system as claimed in claim 17, wherein upon the guidewire colliding with the first oblique shoulder along the guide path of the rotatable inner tube, the guidewire penetrates out of the opening at an angle of about 70°-90° with respect to a horizontal plane.

24. The catheter system as claimed in claim 17, wherein the arcuate opening is at an inclined angle of about 4°-5° with respect to an axial direction of the rotatable inner tube.

25. The catheter system as claimed in claim 17, wherein the distal end of the rotatable inner tube is made of nitinol and the proximal end of the rotatable inner tube is made of metal, and the distal and proximal ends are integrally formed by welding.

26. The catheter system as claimed in claim 17, further comprising:
a support tube, connected to the proximal end of the catheter head.

27. The catheter system as claimed in claim 17, further comprising:
a tip, connected to the distal end of the catheter head.

28. The catheter system as claimed in claim 18, wherein the curved catheter head has an outer diameter of not more than about 0.54 mm and an inner diameter of about 0.48 mm.

29. The catheter system as claimed in claim 18, wherein a maximum vertical height between a top and a bottom of the curved catheter head is not more than about 1 mm.

30. The catheter system as claimed in claim 20, wherein the wings are symmetrically disposed on the opposite sides of the catheter head and the wings become wider and narrower gradually from front to back.

31. The catheter system as claimed in claim 20, wherein a maximum vertical height between the wings and the catheter head is not more than 1.25 mm.

32. The catheter system as claimed in claim 30, wherein a width at a beginning of a distal section of the wings is not more than 0.9 mm and a maximum width of the wings is not more than 2.4 mm.

33. The catheter system as claimed in claim 26, wherein the support tube comprises a three-layer structure including an inner layer, an intermediate layer and an outer layer, wherein the inner layer is formed as a mesh structure and the intermediate layer is formed as a spiral structure.

34. The catheter system as claimed in claim 26, wherein the support tube includes a wall having a thickness of about 0.004 inches.

35. A method for re-entry of a vascular false lumen into a true lumen in a quick, accurate and low-risk way using a catheter head having a lumen, an opening and a first oblique shoulder, and a rotatable inner tube having a distal end with an arcuate opening, the inner tube positioned within the lumen of the catheter head, the method comprising:
rotating the rotatable inner tube to a position where the arcuate opening faces upwards;
inserting a first guidewire into the rotatable inner tube;
pushing the first guidewire to the catheter head, such that the catheter head enters into a region where a total occlusion of the false lumen of the vessel occurs, through a path to the false lumen created by the first guidewire;
pushing a microcatheter until the catheter head passes through the totally occluded region in a straight line, and placing the first oblique shoulder of the catheter head on a position passing through the totally occluded region;
withdrawing the first guidewire;
continually rotating the rotatable inner tube to a position at which the arcuate opening faces downwards;
inserting a second guidewire into the rotatable inner tube; and
pushing the second guidewire to the catheter head, such that the second guidewire penetrates downwards after a collision with the first oblique shoulder on the catheter head, thereby re-entering to the vascular true lumen.

36. The method for re-entry of the vascular false lumen into the true lumen as claimed in claim 35, wherein the first guidewi re has a diameter of about 0.018 inches.

37. The method for re-entry of the vascular false lumen into the true lumen as claimed in claim 35, wherein the second guidewire has a diameter of about 0.014 inches.

38. The method for re-entry of the vascular false lumen into the true lumen as claimed in claim 35, wherein upon the second guidewire colliding with the first oblique shoulder, the second guidewire penetrates out of the opening at an angle of about 70 to about 90 degrees with respect to a horizontal plane.

* * * * *